(12) United States Patent
Noda

(10) Patent No.: US 8,794,832 B2
(45) Date of Patent: Aug. 5, 2014

(54) X-RAY DIAGNOSTIC IMAGING APPARATUS AND X-RAY APPARATUS

(75) Inventor: Koji Noda, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 359 days.

(21) Appl. No.: 12/547,916

(22) Filed: Aug. 26, 2009

(65) Prior Publication Data

US 2010/0054423 A1    Mar. 4, 2010

(30) Foreign Application Priority Data

Sep. 3, 2008  (JP) ................................ P2008-226397

(51) Int. Cl.
*H05G 1/02*    (2006.01)

(52) U.S. Cl.
USPC .......................................... 378/197; 378/193

(58) Field of Classification Search
USPC .................................................. 378/193–198
See application file for complete search history.

(56) References Cited

U.S. PATENT DOCUMENTS

| | | | | |
|---|---|---|---|---|
| 4,501,011 A | * | 2/1985 | Hauck et al. ................... | 378/196 |
| RE34,943 E | * | 5/1995 | Van Endschot et al. ...... | 378/197 |
| 6,431,751 B1 | * | 8/2002 | Everett et al. ................. | 378/197 |
| 2001/0005410 A1 | * | 6/2001 | Rasche et al. ................. | 378/197 |
| 2008/0013690 A1 | * | 1/2008 | Lurz et al. ..................... | 378/167 |
| 2008/0101546 A1 | * | 5/2008 | Delmas et al. ................ | 378/197 |

FOREIGN PATENT DOCUMENTS

JP    2008-000190 A    1/2008

* cited by examiner

*Primary Examiner* — Hoon Song

(74) *Attorney, Agent, or Firm* — Yoshida & Associates, LLC

(57) ABSTRACT

An X-ray generation unit and an X-ray detection unit are held by an arm. Image data is generated based on X-ray projection data which is generated by the X-ray detection unit. A first support member supports the arm and rotates the arm in a first rotation direction. A second support member supports the first support member. The second support member rotates the first support member around a rotation center in a second rotation direction perpendicular to the first rotation direction. A movement unit can move the second support member in an up and down direction.

17 Claims, 8 Drawing Sheets

X-RAY DIAGNOSTIC IMAGING APPARATUS AND X-RAY APPARATUS

CROSS REFERENCE TO RELATED APPLICATION

This application is based upon and claims the benefit of priority from the prior Japanese Patent Application No. 2008-226397, filed on Sep. 3, 2008, the entire contents of which are incorporated herein by reference.

FIELD OF THE INVENTION

The invention relates to an X-ray diagnostic imaging apparatus and an X-ray apparatus which are used to diagnose an object to be examined.

DESCRIPTION OF THE BACKGROUND

Recent years, an X-ray diagnostic imaging apparatus has progressed mainly in a circulatory organ field, with development of an angiographic examination using a catheter or an IVR (Interventional Radiology). Such an X-ray diagnostic imaging apparatus is used in a percutaneous angioplasty, or in a plastic surgery of a congenital cardiac deformity which is combined with a cardiac surgery operation. An application range of an X-ray diagnostic imaging apparatus as an advanced IVR system has been enlarged. An installation environment of an X-ray diagnostic imaging apparatus has been developed from a general catheter room to a complex system called as a hybrid system merged with an operation room.

Japanese patent application publication No. 2008-190 discloses an X-ray diagnostic imaging apparatus for examining circulatory organs of an object. The X-ray diagnostic imaging apparatus is provided with a photographing unit which has a C-shaped arm. Two end portions of the C-shaped arm hold an X-ray generation unit and an X-ray detection unit respectively. The X-ray diagnostic imaging apparatus is further provided with a movement mechanism to move the photographing unit. The object is capable of being photographed from various angles by moving the photographing unit, when the object sits on a bed.

The X-ray diagnostic imaging apparatus is installed in an examination room where facilities enabling a medical treatment or an operation are arranged. When the photographing unit is not used, the photographing unit is separated and recedes from the bed so as not to disturb the medical treatment or the operation. The photographing unit is moved along a rail provided in parallel with a floor of the examination room.

In order to cause the photographing unit to recede from the bed, the examination room requires a larger floor space in the direction of the rail. Accordingly, the examination room needs to include a larger extra space which is not always necessary for the medical treatment or the operation

SUMMARY OF THE INVENTION

An advantage of aspects of the invention is to provide an X-ray diagnostic imaging apparatus and an X-ray apparatus which require a smaller floor space of an examination room.

According to an embodiment of the invention, an X-ray diagnostic imaging apparatus is provided, which includes a first arm, an X-ray generation unit held by the first arm, the X-ray generation unit irradiating X-ray to an object to be examined, an X-ray detection unit held by the first arm, the X-ray detection unit opposing to the X-ray generation unit to detect X-ray emitted from the X-ray generation unit and penetrated through the object, the X-ray detection unit generating X-ray projection data, an image data generation unit to generate image data based on the X-ray projection data which is obtained from the X-ray detection unit, and a mechanism unit to move the first arm, wherein the mechanism unit is provided with a first support member to support the first arm, the first support member rotating the first arm around a rotation center and in a first rotation direction, a second support member to hold the first support member, the second support member rotating the first support member around the rotation center and in a second rotation direction perpendicular to the first rotation direction, and a movement unit to move the second support member in an up and down direction.

According to another embodiment of the invention, an X-ray diagnostic imaging apparatus is provided, which includes a first arm, an X-ray generation unit held by the first arm, the X-ray generation unit irradiating X-ray to an object to be examined, an X-ray detection unit held by the first arm, the X-ray detection unit opposing to the X-ray generation unit to detect X-ray emitted from the X-ray generation unit and penetrated through the object, the X-ray generation unit generating X-ray projection data, and a mechanism unit to move the first arm, wherein the mechanism unit is provided with a first support member to support the first arm, the first support member rotating the first arm around a rotation center and in a first direction, a second support member to hold the first support member, the second support member rotating the first support member around the rotation center and in a second direction perpendicular to the first direction, and a movement unit to move the second support member in an up and down direction.

DETAILED DESCRIPTION OF THE INVENTION

Figure 1:
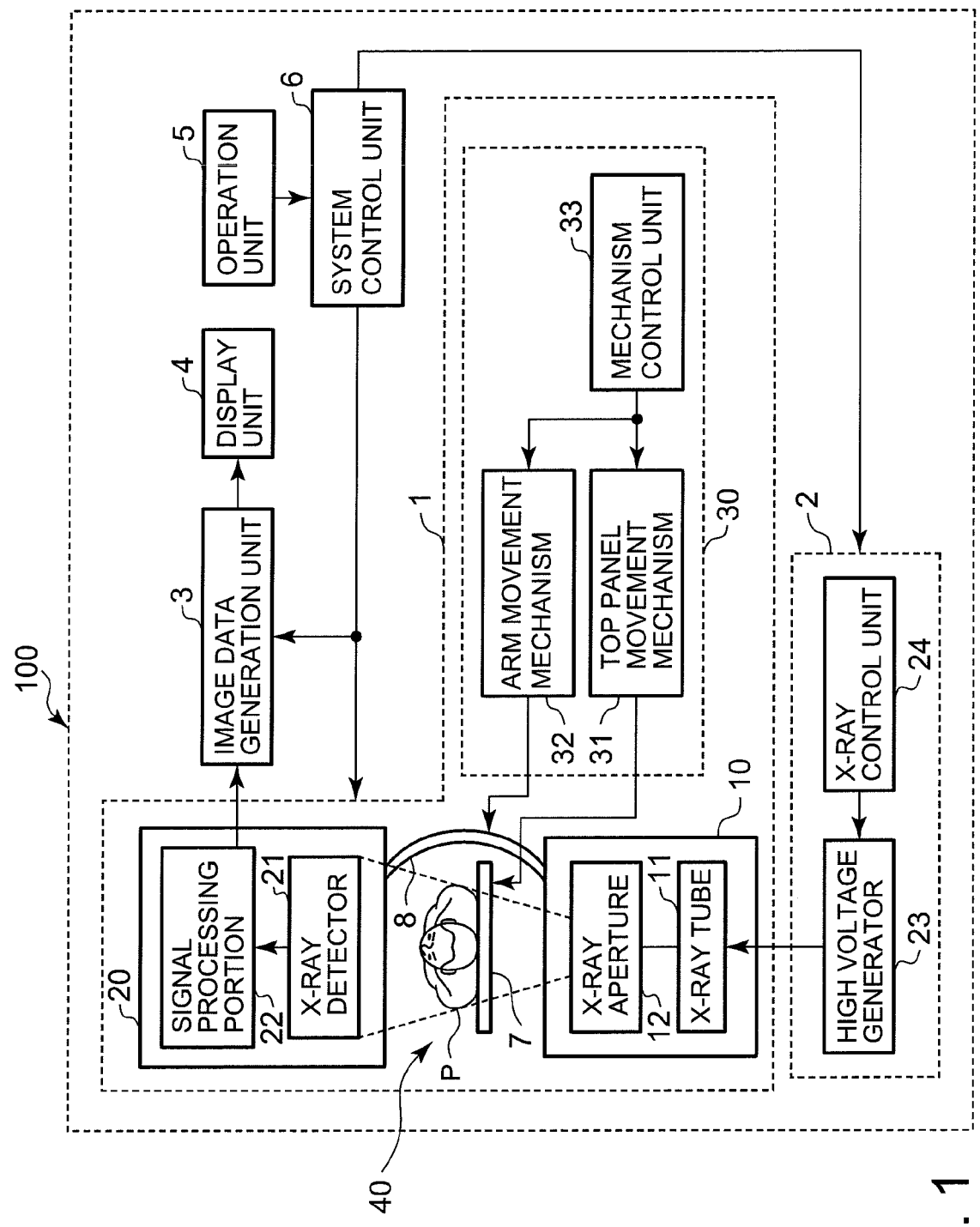
FIG. 1 is a block diagram showing an X-ray diagnostic imaging apparatus according to a first embodiment of the invention.

Hereinafter, embodiments of the invention will be described with reference to the drawings. In the drawings, the same reference numerals designate the same portions, respectively.

An X-ray diagnostic imaging apparatus according to a first embodiment of the invention will be described with reference to FIG. 1 to FIG. 7. FIG. 1 is a block diagram showing an X-ray diagnostic imaging apparatus according to a first embodiment of the invention.

As shown in FIG. 1, an X-ray diagnostic imaging apparatus 100 is provided with an X-ray irradiation/detection section 1, a high voltage generation unit 2, an image data generation unit 3, a display unit 4, an operation unit 5 and a system control unit 6.

The X-ray irradiation/detection section 1 performs X-ray photographing an object P to be examined. The high voltage generation unit 2 generates a high voltage which is necessary for X-ray photographing in the X-ray irradiation/detection section 1. In addition, the image data generation unit 3 generates image data based on X-ray projection data, which is obtained by photographing by the X-ray irradiation/detection section 1.

The display unit 4 displays the image data generated in the image data generation unit 3. The operation unit 5 performs to set a photographing condition including information to identify the object P to be examined, a body position of the object P, region information to be photographed, an examination time and an X-ray irradiation condition. In addition, the operation unit 5 performs to set and to select various conditions with respect to displaying, and performs to input various commands.

The system control unit 6 receives a signal from the operation unit 5. The X-ray irradiation/detection section 1, the high voltage generation unit 2 and the image data generation unit 3 are controlled by the system control unit 6.

The X-ray irradiation/detection section 1 is provided with a top panel 7, an X-ray generation unit 10, an X-ray detection unit 20, a photographing unit 40 and a mechanism unit 30.

The object P sits on the top panel 7. The X-ray generation unit 10 irradiates X-ray to the object P sustained on the top panel 7. The X-ray detection unit 20 detects X-ray penetrated through the object P by irradiation of X-ray from the X-ray generation unit 10. The X-ray detection unit 20 generates X-ray projection data. The photographing unit 40 is composed of a first arm 8 to hold the X-ray generation unit 10 and the X-ray detection unit 20. The mechanism unit 30 moves the top panel 7 and the first arm 8.

The X-ray generation unit 10 is provided with an X-ray tube 11 and an X-ray aperture 12. The X-ray tube 11 generates X-ray. The X-ray aperture 12 is arranged between the X-ray tube 11 and the object P. The X-ray aperture 12 limits the irradiation range of the X-ray emitted from the X-ray tube 11 and irradiated to the object P.

The X-ray detection unit 20 is provided with an X-ray detector 21 and a signal processing portion 22. The X-ray detector 21 is arranged opposite to the X-ray generation unit 10. The X-ray detector 21 detects the X-ray penetrated through the object P and converts the X-ray to an electrical signal. The signal processing portion 22 processes the electrical signal converted in the X-ray detector 21, and generates X-ray projection data.

Figure 7:
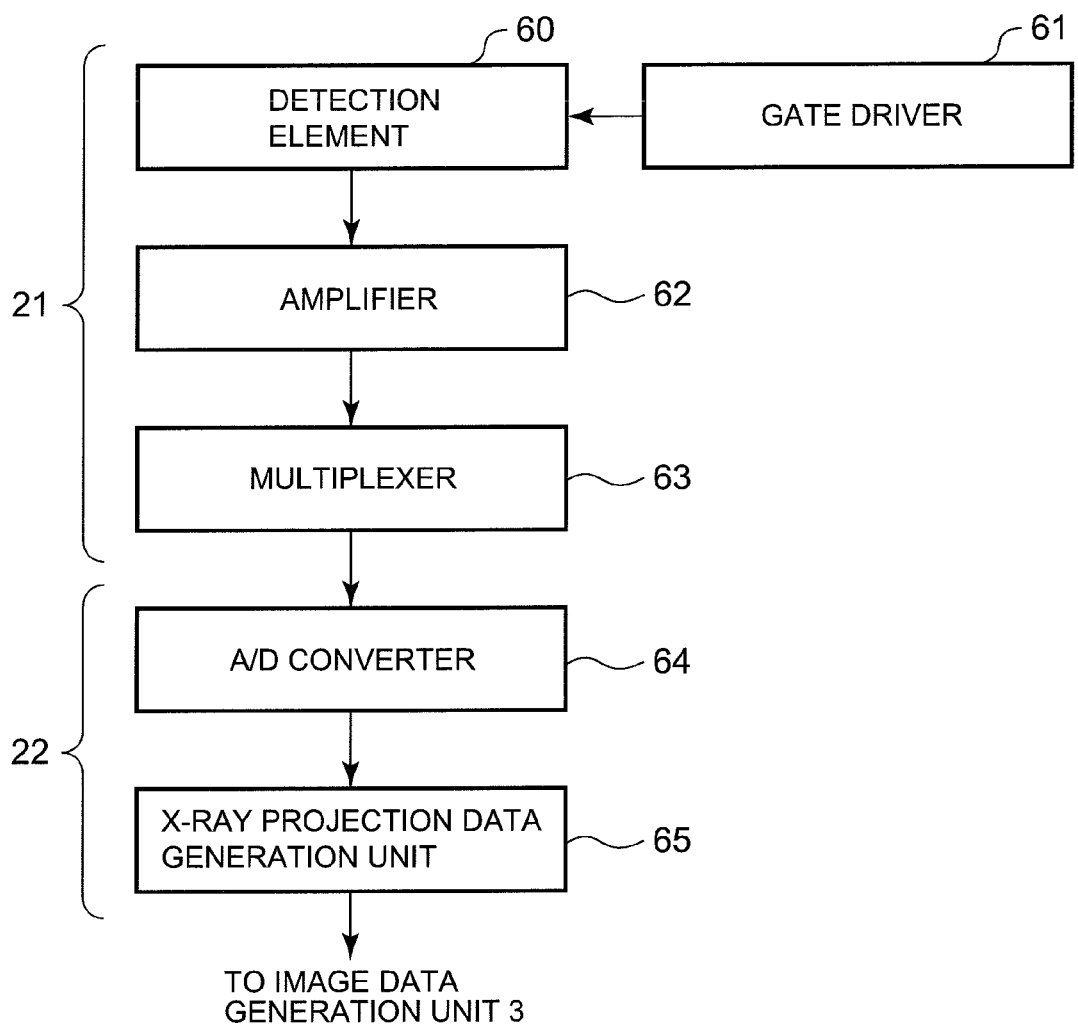
FIG. 7 is a block diagram showing the construction of an X-ray detection unit shown in FIG. 1

The X-ray detector 21 and the signal processing portion 22 are configured as shown in FIG. 7. The X-ray detector 21 has a detection element 60 composed of a plurality of elements arranged on a line. The X-ray inputted to the detection element 60 are converted to an electrical charge by the detection element 60. A gate driver 61 provides a driving pulse to the detection element 60 to read out the electrical charge. The electrical charge read out from the detection element 60 is converted to an voltage by an amplifier 62. Signal outputted from the amplifier 62 is selected for each line by a multiplexer 63.

An analog signal outputted from the multiplexer 63 is converted to a digital signal by an A/D converter 64 which is provided in the signal processing portion 22. The digital signal outputted from the A/D converter is inputted to an X-ray projection data generation unit 65. The X-ray projection data generation unit 65 generates X-ray projection data for each line. The X-ray projection data generated by the X-ray projection data generation unit 65 is outputted to the image data generation unit 3 shown in FIG. 1.

The X-ray detection unit 20 may be composed of an image intensifier, a television camera and an A/D converter. The image intensifier converts inputted X-ray into light. The television camera photographs the light from the image intensifier, and outputs an electrical signal. The A/D converter converts the electrical signal obtained from the television camera into a digital signal.

The mechanism unit 30 is provided with a top panel movement mechanism 31, an arm movement mechanism 32 and a mechanism control unit 33.

The top panel movement mechanism 31 moves the top panel, on which the object P is sustained, to a position between the X-ray generation unit 10 and X-ray detection unit 20 so that X-ray photographing of the object P can be performed. The top panel movement mechanism 31 moves the top panel 7 in the longitudinal direction, in the width direction or in the up and down direction. The arm movement mechanism 32 moves the first arm 8. The mechanism control unit 33 controls the top panel movement mechanism 31 and the arm movement mechanism 32.

The arm movement mechanism 32 moves the first arm 8 to set the X-ray generation unit 10 and the X-ray detection unit 20 at an angle and a height where to X-ray photographing of the object P can be performed. When examination of the object P is completed and when the photographing unit 40 is not necessary to use until next examination, the arm movement mechanism 32 moves the first arm 8 to a recede position The high voltage generation unit 2 is provided with a high voltage generator 23 and an X-ray control unit 24.

The high voltage generator 23 supplies a high voltage to the X-ray tube provided in the X-ray generation unit 10. The high voltage generator 23 supplies a high voltage and a heating voltage to the X-ray tube 11, based on a control signal for the X-ray irradiation condition, which is provided from the X-ray control unit 24. The high voltage is used to generate X-ray for a fluoroscopic use and X-ray for a photographic use. The energy of the X-ray for a photographic use is higher than the energy of the X-ray for the fluoroscopic use.

The X-ray control unit 24 controls the high voltage generator 23 based on information as to the X-ray irradiation condition, which is included in the photographing condition and is provided from the system control unit 6. The X-ray irradiation condition contains such information as a tube voltage and a tube current.

The X-ray control unit 24 sets the tube voltage and current for the fluoroscopic and photographic use, by controlling the supplying voltage and the heating voltage which are generated by the high voltage generator 23.

The image data generation unit 3 generates image data such as fluoroscopic image data and photographic image data, based on the X-ray projection data outputted for each line from the signal processing portion 22 of the X-ray detection unit 20. The image data generation unit 3 outputs the generated image data to the display unit 4.

The display unit 4 is provided with a liquid crystal panel or a CRT monitor. The display unit 4 displays the image data outputted from the image data generation unit 3.

The operation unit 5 is an interactive interface, which is provided with an input device such as a key board, a trackball, a joystick or a mouse. The operation unit 5 is further provided with a display panel and switches of various types.

The system control unit 6 is provided with a CPU and a memory circuit. The system control unit 6 stores inputted information such as a command signal and the photographing condition supplied from the operation unit 5. Then, the system control unit 6 controls the X-ray diagnostic imaging apparatus 100 totally based on the stored inputted information.

The X-ray irradiation/detection section is installed in an examination room covered by a shielding material to prevent the X-ray from leaking outside. In the examination room, X-ray photographing is performed for an examination, a medical treatment, or an operation. A medical treatment or an operation is performed after an examination is finished by carrying out X-ray photographing and after the first arm 8 is moved to and is positioned at a recede position subsequently, as will be described later.

Figure 2:
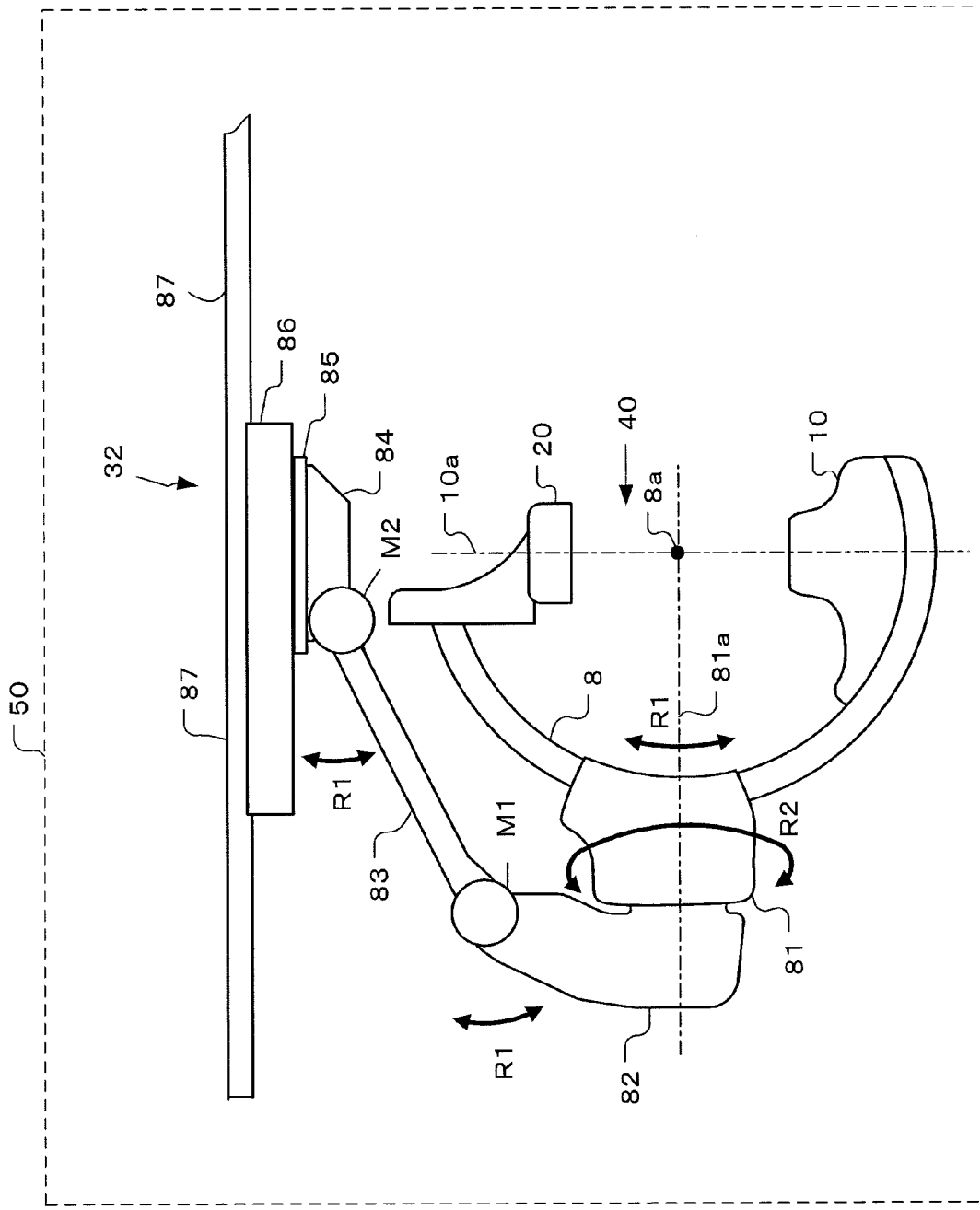
FIG. 2 is a front view showing a structure of an arm movement mechanism shown in FIG. 1
Figure 3:
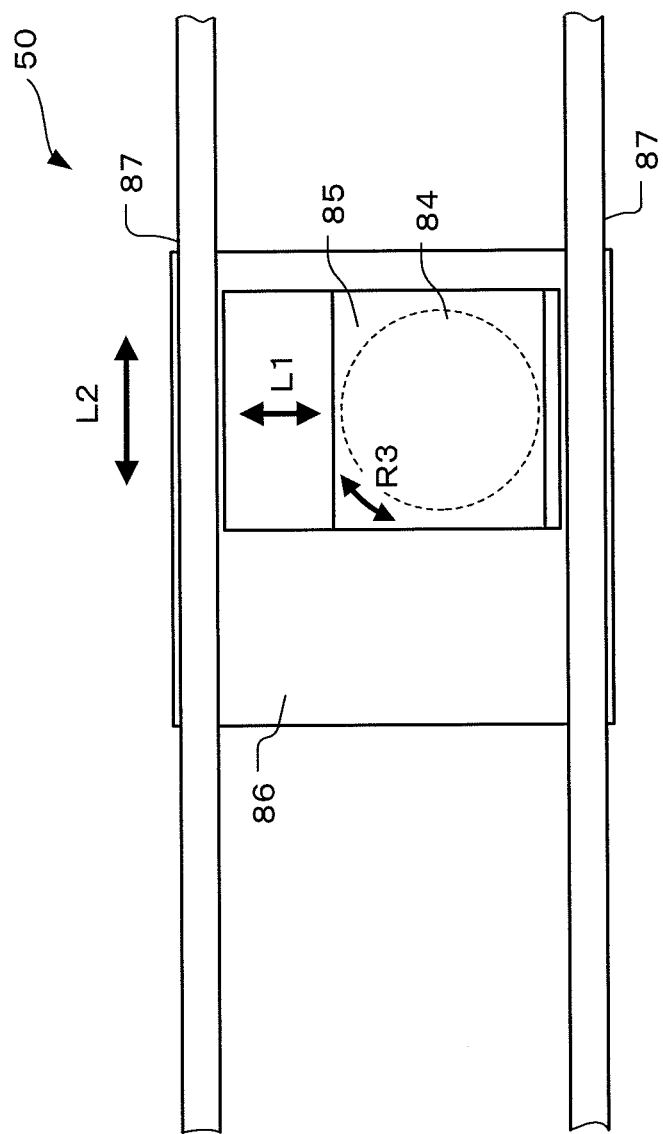
FIG. 3 is a plane view of a portion of the arm movement mechanism seen from above.

The structure and the operation of the arm movement mechanism 32 of the mechanism unit 30 of FIG. 1 will be described. FIG. 2 is a front view showing the structure of the arm movement mechanism 32. FIG. 3 is a plane view of a portion of the arm movement mechanism seen from above.

As shown in FIG. 2, the arm movement mechanism 32 installed in an examination room 50 is provided with a first and a second support members 81, 82, a ceiling support member including a third to a fifth support members 84 to 86, a second arm 83 and guide rails 87, 87. In FIG. 3, the guide rails 87, 87 are separated from each other and extend in parallel. The guide rails 87, 87 are arranged horizontally to a ceiling of the examination room 50.

In FIG. 2, the first support member 81 supports the first arm 8 rotatably. The second support member 82 supports the first support member 81 rotatably. The second arm 83 supports the second support member 82 rotatably. The third support member 84 supports the second arm 83 to allow the second arm 83 to tilt. The fourth support member 85 supports the third support member 84 rotatably. The fifth support member 86 supports the fourth support member 85 to allow the fourth support member 85 to slide. The guide rails 87, 87 supports the fifth support member 86 movably.

The first arm 8 is C-shaped and has two end portions. The X-ray generation unit 10 is held by one of the two end portions. The X-ray detection unit 20 is held by the other of the two end portions.

The first support member 81 houses a motor to drive and rotate the first arm 8. On a back side of the first arm 8, a belt (not shown) is arranged along the first arm 8. End portions of the belt are fixed to the end portions of the first arm 8, respectively. The belt can be rolled up by driving the motor.

The first arm 8 is rotated around a rotation center (a point) 8*a* and in a direction shown by an arrow R1. The rotation center 8*a* is located on a virtual straight line 10*a* which passes through the centers of the X-ray generation unit 10 and the X-ray detection unit 20.

The second support member 82 is L-shaped and is provided with two end portions. One of the end portions of the second support member 82 supports the first support member 81. The second support member 82 houses a motor to drive the first support member 81. The rotation of the motor is transmitted to the first support member 81 via chains and a decelerator.

The motor of the second support member 82 rotates the first support member 81 around the rotation center 8*a* and in a direction shown by an arrow R2. The direction is a perpendicular direction to the direction R1. In other words, the first support member 81 rotates around a virtual straight line 81*a*, which is orthogonal to the straight line 10*a* at the rotation center 8*a*.

The second arm 83 is provided with two end portions. One of the end portions of the second arm 83 supports the other of the end portions of the second support member 82. The one of the end portions of the second arm 83 houses a motor to which a cover M1 is attached.

The rotation of the motor of the second arm 83 is decelerated by a decelerator and is transmitted to the second support member 82. The second arm 83 rotates the second support member 82 around an axis of rotation provided at the one of the end portions of the second arm 83. In addition, the second arm 83 rotates the second support member 82 in the same direction R1 as the rotation direction of the first arm 8.

The third support member 84 houses a motor to which a cover M2 is attached. The rotation of the motor of the third support member 84 is decelerated by a decelerator and is transmitted to the second arm 83 arranged at the lower side of the third support member 84. By transmitting the rotation of the motor of the third support member 84, the second arm 83 is tilted in the direction R1. As a result, the second support member 82 is moved in an up and down direction by rotation of the motors provided in the second arm 83 and the third support member 84.

The fourth support member 85 supports the third support member 84 arranged on a lower side of the fourth support member 85. The fourth support member 85 houses a motor to drive and rotate the third support member 84. Further, as shown in FIG. 3, the fourth support member 85 rotates the third support member 84 in a direction shown by an arrow R3 that is a horizontal direction.

As shown in FIG. 2 and FIG. 3, the fifth support member 86 supports the fourth support member 85. The fifth support member 86 houses a motor. The rotation of the motor of the fifth support member 86 is transmitted to a pinion gear provided in the fourth support member 85 via a rack in order to drive the fourth support member 85. As a result, the fourth support member 85 is moved in a direction shown by an arrow L1 that is a horizontal direction, as shown in FIG. 3.

The fifth support member 86 houses a motor which allows self-propelling of the fifth support member 86. As described above, the two guide rails 87, 87 are arranged horizontally to the ceiling of the examination room 50. The fifth support member 86 is engaged with the guide rails 87, 87. The rotation of the motor of the fifth support member 86 is decelerated by a decelerator. The rotation force of the motor of the fifth support member 86 acts on the guide rails 87, 87. By the action of the rotation force, as shown in FIG. 3, the fifth support member 86 is moved along the guide rail 87 in a direction shown by an arrow L2, which is a direction perpendicular to the direction L1.

Figure 4B:
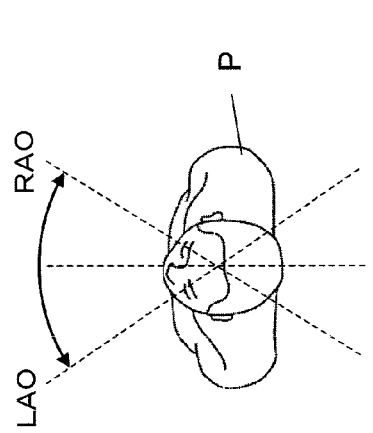
FIG. 4B and FIG. 4C show directions of X-ray photographing which are controlled by the arm movement mechanism.
Figure 4C:
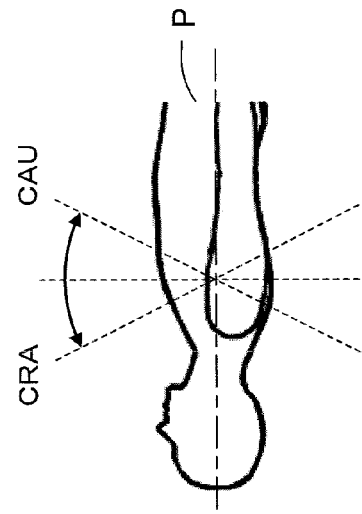
Figure 4A:
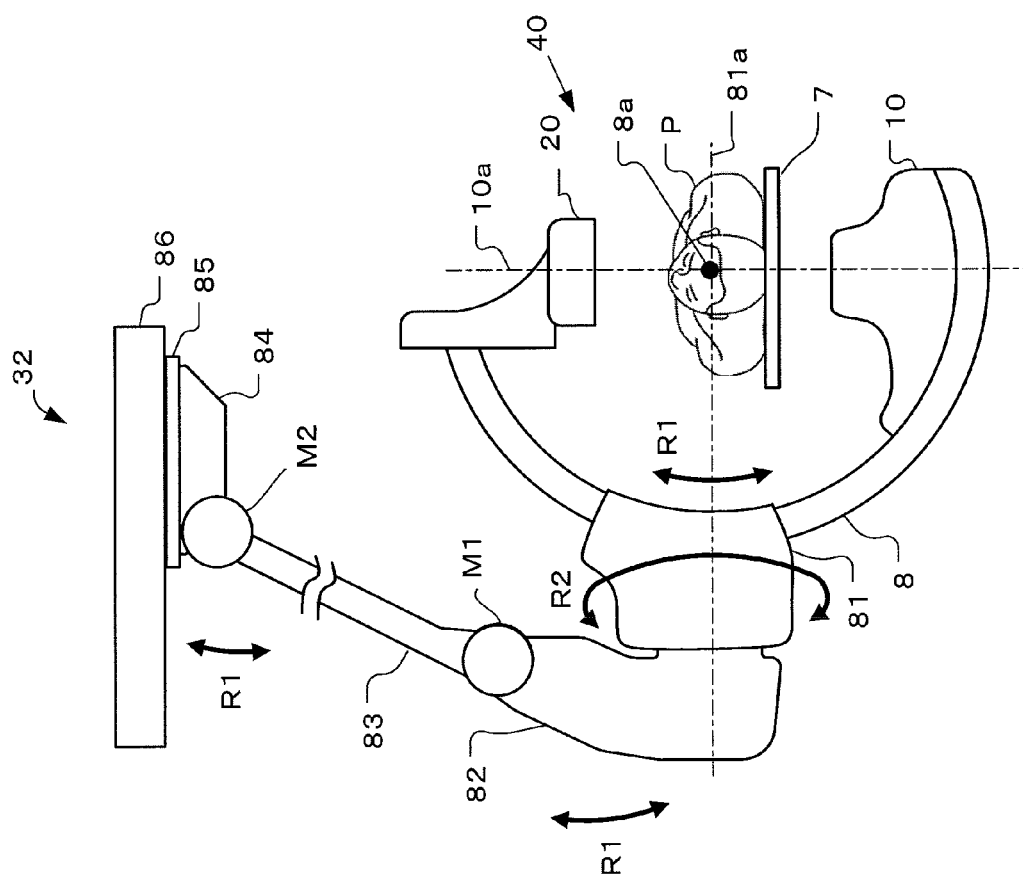
FIG. 4A is a diagram to explain movement of arms moved by the arm movement mechanism.

FIGS. 4A to 4C are diagrams to describe the movement of the first arm 8 at the time of X-ray photographing. At a first stage, the top panel, which sustains the object P, is not positioned between the X-ray generation unit 10 and the X-ray detection unit 20 but at a position apart from the unit 10, 20 in the horizontal direction, as shown in FIG. 4A. When X-ray photographing is performed, the third support member 84 of the arm movement mechanism 32 tilts the second arm 83 (in the downward direction) from the position shown in FIG. 2, for example, to the position shown in FIG. 4A. By tilting the second arm 83, the second arm 83 moves the second support member 83 downward as shown in FIG. 4A.

Concurrently with the movement of the second support member 82, or after the movement of the second support member 82, the second arm 83 rotates the second support member 82 in the direction R1 (in the opposite direction to the tilt of the second arm 83). The second arm 83 stops rotation at an angle where the straight line 81*a* becomes horizontal.

Further, concurrently with the rotation of the second support member 82, or after the rotation of the second support member 82, the second support member 82 rotates the first support member 81 in the direction R2. The second support member 82 stops rotation at an angle where the first arm 8 becomes in the vertical direction to the ceiling.

In addition, concurrently with the rotation of the first support member 81, or after the rotation of the first support member 81, the first support member 81 rotates the first arm 8 in the direction R1 and stops the rotation at an angle where the straight line 10a become vertical.

After the rotation of the first arm 8, the top panel movement mechanism 31 moves the top panel sustaining the object P to a position between the X-ray generation unit 10 and the X-ray detection unit 20 as shown in FIG. 4A.

After moving the top panel 7, the third support member 84 tilts the second arm 83 in the up and down direction. The second arm 83 rotates the second support member 82 and moves the rotation center 8a in the up and down direction. The rotation center 8a is an iso-center that is a center point, which is a target for X-ray irradiation. By the movement of the rotation center 8a in the up and down direction, the rotation center 8a is set to a height of a region of the object P to be photographed. The fifth support member 86 moves the fourth support member 85 in the direction L1 shown in FIG. 3. Further, the fifth support member 86 runs along the guide rails 87, 87 in the direction L2. As a result, the position of the iso-center is adjusted in the horizontal direction, and the iso-center is set at the region of the object P to be photographed.

The region of the object P to be photographed may be set to an iso-center, by performing tilt of the second arm 83 and rotation of the second support member 82 at the same time when the top panel 7 is moved. The region of the object P to be photographed may be set to the iso-center without moving the second arm 83 and the second support member 82 but by moving the top panel 7.

After setting the iso-center to the region of the object P to be photographed, the first support member 81 rotates the first arm 8 in the direction R1. By the rotation of the first arm 8, the X-ray generation unit 10 and the X-ray detection unit 20 is rotated from a right oblique direction RAO to a left oblique direction LAO or the reverse, as shown in FIG. 4B. In addition, the second support member 82 rotates the first support member 81 in the direction R2. By the rotation of the first support member 81, the X-ray generation unit 10 and the X-ray detection unit 20 are rotated from a head region direction CRA to a foot region direction CAU or the reverse, as shown in FIG. 4C. By these rotations, the object P can be X-ray photographed from an arbitrary angle.

As described above, by moving the second support member 82 in the up and down direction in addition to the movement of the top panel 7 in the up and down direction, the first arm 8 can be moved extensively in the up and down direction. Thus, the range of a position to set an iso-center can be enlarged so that the iso-center can be positioned at an arbitrary height which allows easy working for an examination, a medical treatment or an operation. As a result, burden of the medical staff such as an operator to operate the X-ray diagnostic imaging apparatus 100 may be reduced. The operation efficiency of the medical staff may be improved.

Figure 5:
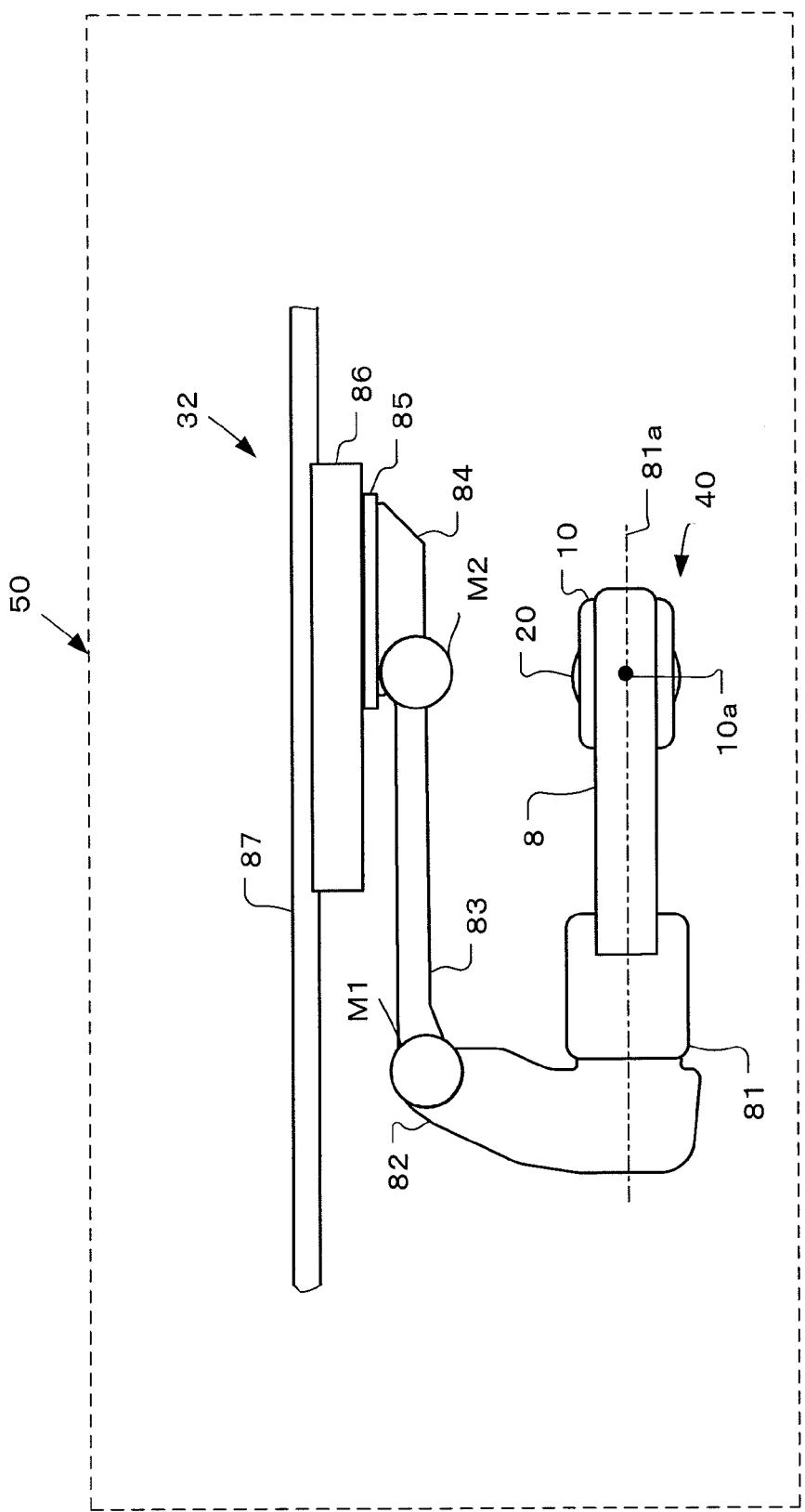
FIG. 5 shows a recede state of the arms moved by the arm movement mechanism.
Figure 6:
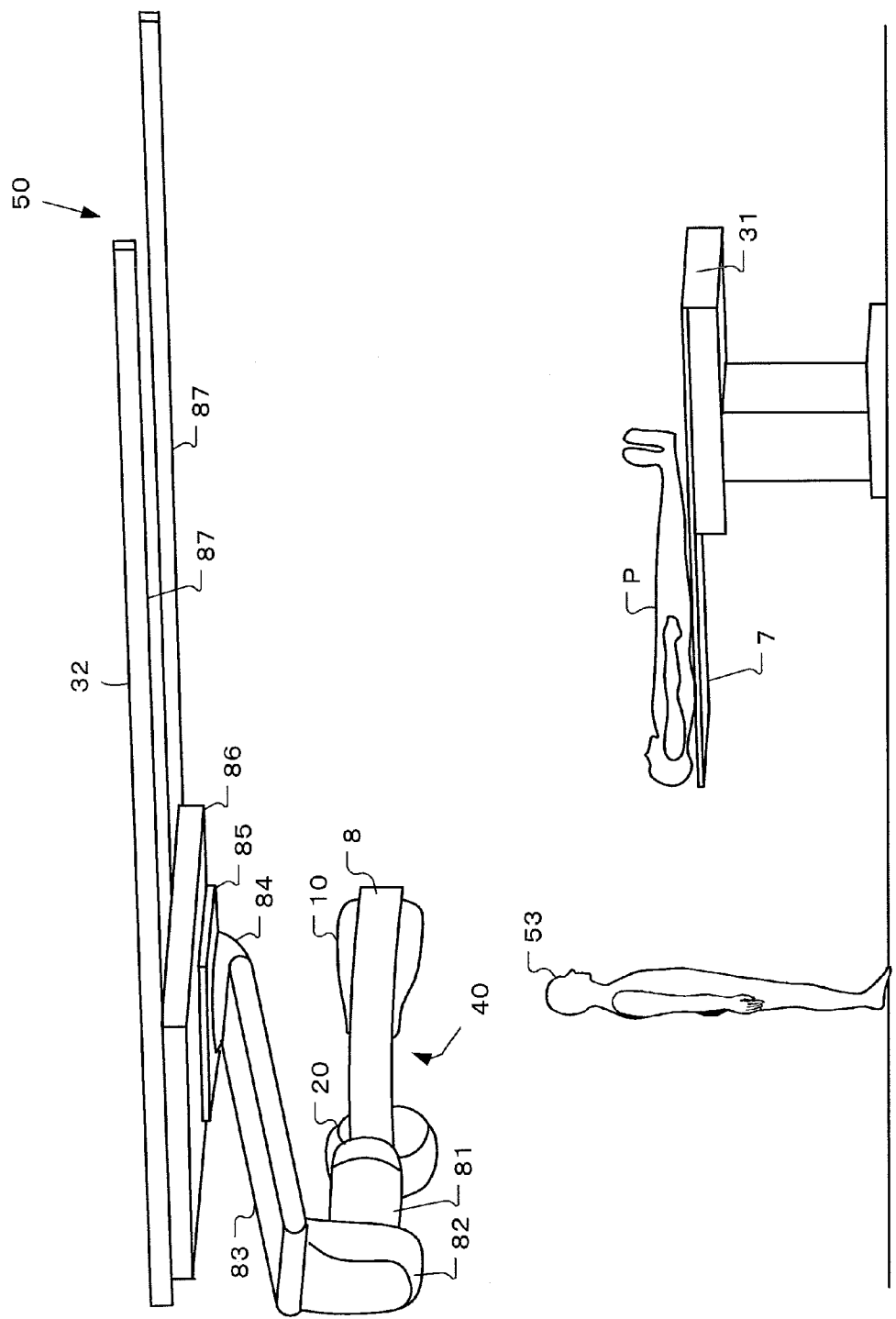
FIG. 6 shows a layout in an examination room at the recede state of the arms.

Hereinafter, a receding operation of the first arm 8 will be described. The receding operation is carried out after X-ray photographing is completed. FIG. 5 shows the situation that the first arm 8 shown in FIG. 4A recedes. FIG. 6 shows the situation of the examination room 50 where the first arm 8 recedes.

The receding operation of the first arm 8 is performed by pushing a recede button provided in the operation unit 5 to work the arm movement mechanism 32. By pushing the recede button, a computer (not shown) operates. The arm movement mechanism 32 is controlled automatically by a computer program stored in the computer so that the first arm 8 can be moved to a recede position.

After the X-ray photographing is completed under the state shown in FIG. 4A, the top panel movement mechanism 31 moves the top panel 7 to a position such as a medical treatment position, an operation position or a position which is easy for the object P to get on and off. The position is apart from the X-ray generation unit 10 and X-ray detection unit 20.

After the movement of the top panel 7, the second support member 82 rotates the first support member 81 in the direction R2, and stops the first support member 81 at an angle where the straight line 10a becomes horizontal.

Concurrently with the rotation of the first support member 81, or after the rotation of the first support member 81, the third support member 84 tilts the second arm 83 in an upward direction. By tilting the second arm 83, the second support member 82 is moved in the upward direction. The second arm 83 is stopped at a position where the one of the two end portions of the second arm 83 reaches a top dead point.

As described above, the second arm 83 is tilted at the same time as the first support member 81 is rotated, in the case the second support member 82 is moved in the upward direction concurrently with the rotation of the first support member 81. As a result, during the receding action of the first arm 8, the X-ray detection unit 20, which is positioned upper than the X-ray generation unit 10, can be prevented from interfering or colliding with the second arm 83.

Concurrently with the tilt of the second arm 83, or after the tilt of the second arm 83, the second arm 83 rotates the second support member 82 in the direction R1 shown in FIG. 4A. The rotation of the second support member 82 is stopped at an angle where the straight line 81a becomes horizontal as shown in FIG. 5. With the stop of the second support member 82, the arm movement mechanism 32 finishes the action to move the first arm 8 to the recede position.

As shown in FIG. 6, in a recede state, the first arm 8 and the arm movement mechanism 32 are positioned upward the medical staff 53. The second arm 83 of the arm movement mechanism 32 is stopped at a position where the one of the two end portions of the second arm 83 reaches the top dead point located near the guide rails 87, 87. The first and second support members 81, 82 are stopped at an angle where the first arm 8 becomes approximately horizontal.

In the recede state, a free space located downward the first arm 8 and the arm movement mechanism 32 may be utilized as a working space for the medical staff 53, because the first arm 8 and the arm movement mechanism 32 are positioned upward the medical staff 53. Thus, a working space for the medical staff 53 may be ensured without enlarging the floor space of the examination room 50 where the X-ray irradiation/detection section 1 is installed.

Figure 8:
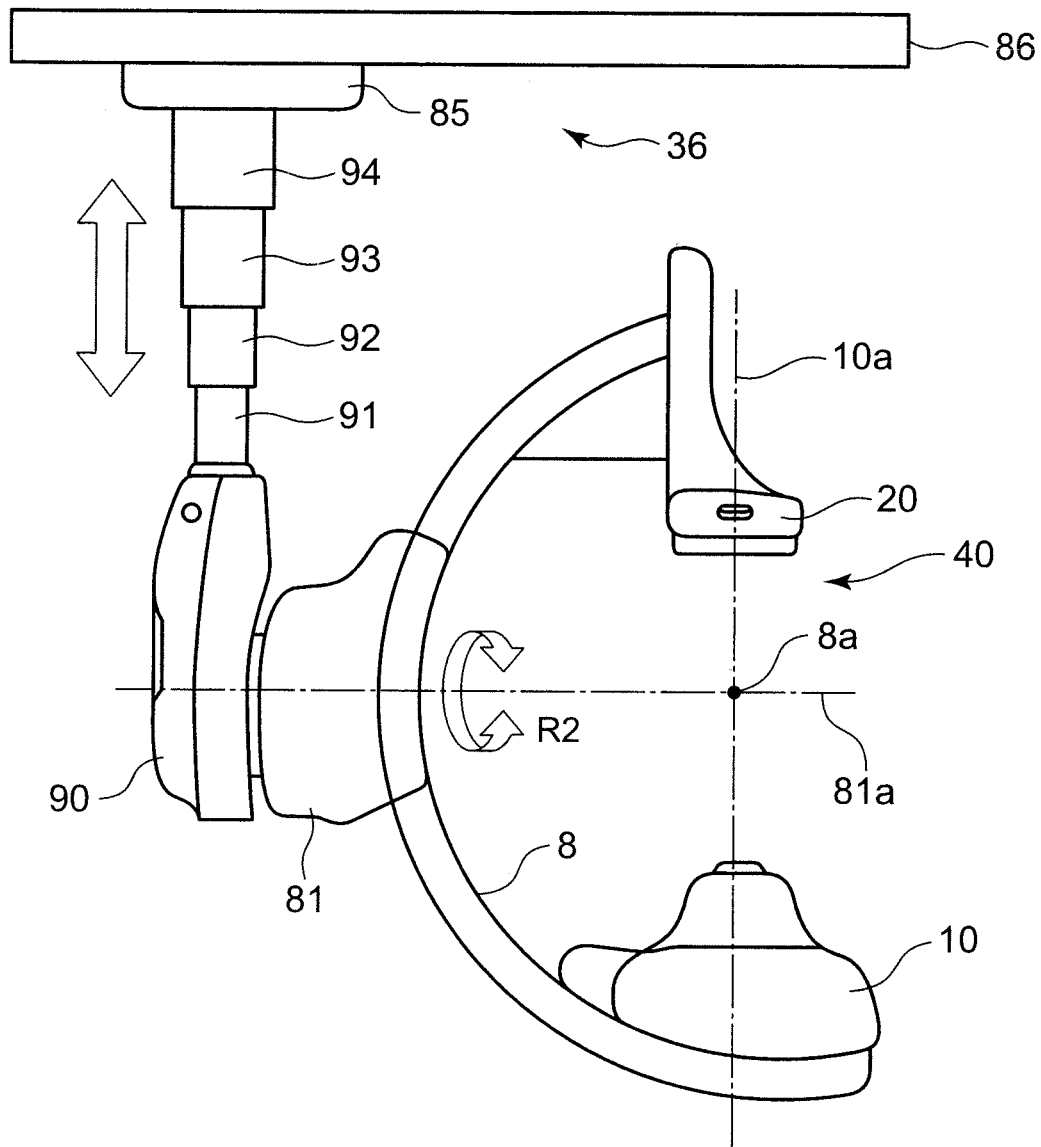
FIG. 8 is a front view showing a structure of another arm movement mechanism according to a second embodiment of the invention.

FIG. 8 is a front view showing a structure of another arm movement mechanism according to a second embodiment of the invention.

An arm movement mechanism 36 is provided with a first support member 81, a second support member 90, third support members 91 to 94, a fourth support member 85, a fifth support member 86 and two guide rails (not shown). The structure and action of the first support member 81, the fourth support member 85, the fifth support member 86 and the guide rails are the same as those described in the first embodiment. The third supports 91 to 94 are cylindrical. The diameters of the supports 91 to 94 are different.

The photographing unit 40 is provided with the X-ray generation unit 10, X-ray detection unit 20 and the first arm 8 to hold the X-ray generation unit 10 and the X-ray detection unit 20. The first support member 81, which constitutes the arm movement mechanism 36, supports the first arm 8.

The second support member 90 houses a motor. Rotation of the motor is transmitted to the first support member 81 via a decelerator to rotate the first support member 81 in a direction shown by the arrow R2. The third support member 90 is held by third support member 91.

The third support member 92 can hold the third support member 91 under the state that the third support member 91 is extended downward. The third support member 91 can be put in the third support member 92 by pulling up the third support member 91. The third support member 93 can hold the third support member 92 under the state that the third support member 92 is extended downward. The third support member 92 can be put in the third support member 93 by pulling up the third support member 92.

The third support member 94 can hold the third support member 93 under the state that the support 93 is extended downward. The third support member 93 can be put in the third support member 94 by pulling up the third support member 93. The fourth support member 85 holds the third support member 94.

A receding operation, which recedes the first arm 8 after completion of X-ray photographing, will be described. The third support member 90 rotates the first support member 81 in the direction shown by the arrow R2, and stops the first support member 81 at an angle where the straight line 10a becomes horizontal. By pulling up the third support members 91-93 and put in third support members 92 to 94 respectively, the photographing unit 40 can recede in the upward direction.

Other embodiments or modifications of the present invention will be apparent to those skilled in the art from consideration of the specification and practice of the invention disclosed herein. It is intend portioned that the specification and example embodiments be considered as exemplary only, with a true scope and spirit of the invention being indicated by the following.

What is claimed is:

1. An X-ray diagnostic imaging apparatus, comprising:
a first arm;
an X-ray generation unit held by the first arm, the X-ray generation unit irradiating X-ray to an object to be examined on a top panel;
an X-ray detection unit held by the first arm, the X-ray detection unit opposing to the X-ray generation unit to detect X-ray emitted from the X-ray generation unit and penetrated through the object, the X-ray detection unit generating X-ray projection data;
an image data generation unit to generate image data based on the X-ray projection data which is obtained from the X-ray detection unit; and
a mechanism unit to move the first arm,
wherein the mechanism unit is provided with
a first support member to support the first arm, the first support member rotating the first arm around a rotation center and in a first rotation direction,
a second support member to hold the first support member, the second support member rotating the first support member around the rotation center and in a second rotation direction perpendicular to the first rotation direction, and
a second arm having two end portions, one of the end portions supporting the second support member, the second arm rotating the second support member in the same direction as the first rotation direction and moving the second support member in an up and down direction, and
a third support member arranged to support the other of the end portions of the second arm, the third support member tilting the second arm in an up and down direction such that the second arm is not positioned to project beyond the second support member in a direction where the one of the end portions is seen from the other of the end portions, and
wherein the mechanism unit is configured to move the first support member and the second support member in an up and down direction at the same time when the top panel is moved in an up and down direction, and is configured to receive a receding instruction in receding operation, so that the first arm is rotated and is stopped at an angle where the first arm becomes approximately horizontal by a receding operation of the first arm and further that the second arm is moved in an upward direction and is stopped at a position where the second arm reaches a receding position.

2. The X-ray diagnostic imaging apparatus according to claim 1, wherein:
the first arm is C-shaped and is provided with two end portions, one of the end portions of the first arm holding the X-ray generation unit, the other of the end portions of the first arm holding the X-ray detection unit.

3. The X-ray diagnostic imaging apparatus according to claim 1,
wherein the mechanism unit is further provided with a fourth support member to support the third support member, and the fourth support member rotates the third support member in a third rotation direction perpendicular to the first and the second rotation directions.

4. The X-ray diagnostic imaging apparatus according to claim 3,
wherein the mechanism unit is further provided with a fifth support member and a guide rail, the fifth support member supporting the fourth support member, the guide rail being engaged with the fifth support member and being arranged to extend horizontally; and
wherein the fifth support member moves the fourth support member in a horizontal direction, and the fifth support member can be moved along the guide rail in a direction perpendicular to a moving direction of the fourth support member.

5. The X-ray diagnostic imaging apparatus according to claim 1, further comprising a top panel to sustain the object, wherein a height of an iso-center is set by moving the top panel and the first arm in the up and down direction.

6. The X-ray diagnostic imaging apparatus according to claim 1, wherein rotation of the first support member and tilting movement of the second arm are performed at the same time so that the second support member can be caused to move upward concurrently with the rotation of the first support member, in a receding action of the first arm.

7. An X-ray apparatus, comprising:
a first arm;
an X-ray generation unit held by the first arm, the X-ray generation unit irradiating X-ray to an object to be examined on a top panel;
an X-ray detection unit held by the first arm, the X-ray detection unit opposing to the X-ray generation unit to detect X-ray emitted from the X-ray generation unit and penetrated through the object, the X-ray detection unit generating X-ray projection data; and a mechanism unit to move the first arm, wherein the mechanism unit is provided with a first support member to support the first arm, the first support member rotating the first arm around a rotation center and in a first rotation direction, a second support member to hold the first support member, the second support member rotating the first support member around the rotation center and in a second rotation direction perpendicular to the first rotation direction, and a second arm having two end portions, one of the end portions supporting the second support member, the second arm rotating the second support member in the same direction as the first rotation direction and moving the second support member in an up and down direction, and a third support member arranged to support the other of the end portions of the second arm, the third support member tilting the second arm in an up and down direction such that the second arm is not positioned to project beyond the second support member in a direction where the one of the end portions is seen from the other of the end portions, and wherein the mechanism unit is configured to receive a receding instruction in receding operation so that the first arm is rotated and is stopped at an angle where the first arm becomes approximately horizontal and further that the second arm is moved in an upward direction and is stopped at a position where the second arm reaches a receding position.

8. The X-ray apparatus according to claim 7, wherein:
the first arm is C-shaped and is provided with two end portions, one of the end portions of the first arm holding the X-ray generation unit, the other of the end portions of the first arm holding the X-ray detection unit.

9. The X-ray apparatus according to claim 7, wherein:
the mechanism unit is further provided with a fourth support member to support the third support member, and the fourth support member rotates the third support member in a third direction perpendicular to the first and the second directions.

10. The X-ray apparatus according to claim 9,
wherein the mechanism unit is further provided with a fifth support member and a guide rail, the fifth support member supporting the fourth support member, the guide rail being engaged with the fifth support member and being arranged to extend horizontally; and
wherein the fifth support member moves the fourth support member in a horizontal direction, and the fifth support member can be moved along the guide rail in a direction perpendicular to a moving direction of the fourth support member.

11. The X-ray apparatus according to claim 7,
wherein rotation of the first support member and tilting movement of the second arm are performed at the same time so that the second support member can be caused to move upward concurrently with the rotation of the first support member, in a receding action of the first arm.

12. An X-ray apparatus mountable on a ceiling wall, comprising:
a ceiling support member mounted on the ceiling wall;
a first arm for mounting an X-ray generation unit that irradiates X-ray to an object to be examined and an X-ray detection unit that opposes the X-ray generation unit for detecting the X-ray emitted from the X-ray generation unit and penetrated through the object;
a first support member for rotatably supporting the first arm around a rotation center along a first rotation direction;
a second support member having L-shape for rotatably supporting the first support member at one end of the L-shape around the rotation center along a second rotation direction that is perpendicular to the first rotation direction, the second support member at the other end of the L-shape being rotatably supported around the rotation center along the first rotation direction;
a second arm for rotatably supporting the second support member at one end and the X-ray apparatus at the other end via the ceiling support member, wherein the mechanism unit is configured to receive a receding instruction in receding operation; and
a mechanism unit is configured to move the first arm, so that the first arm is rotated and is stopped at an angle where the first arm becomes approximately horizontal and further that the second arm is moved in an upward direction and is stopped at a position where the second arm reaches a receding position.

13. The X-ray apparatus mountable on a ceiling wall according to claim 12, the ceiling support member further comprising:
a third support member for rotatably supporting the second arm; and
a fourth support member for rotatably supporting the third support member in a third rotational direction that is perpendicular to the first rotational direction and the second rotational direction.

14. The X-ray apparatus mountable on a ceiling wall according to claim 13, the ceiling support member further comprising:
a fifth support member for supporting the fourth support member; and
a guide rail engaged with the fifth support member so as to slide the fourth support member in a horizontal direction on a predetermined plane.

15. The X-ray apparatus mountable on a ceiling wall according to claim 14,
wherein the fourth support member additionally moves in a direction perpendicular to the horizontal direction on the same predetermined plane.

16. The X-ray apparatus mountable on a ceiling wall according to claim 12,
wherein the first arm and the second arm are substantially parallel with each other at a predetermined receded position.

17. The X-ray apparatus according to claim 12, wherein the ceiling support member further includes:
a third support member arranged to support the other end of the second arm, the third support member tilting the second arm in an up and down direction;
a fourth support member to support the third support member, the fourth support member rotating the third support member in a third rotation direction perpendicular to the first and the second rotation directions; and
a fifth support member and a guide rail, the fifth support member supporting the fourth support member, the guide rail being engaged with the fifth support member and being arranged to extend horizontally,
the fifth support member moving the fourth support member in a horizontal direction, the fifth support member being able to be moved along the guide rail in a direction perpendicular to a moving direction of the fourth support member.

* * * * *